(12) United States Patent
Iguchi et al.

(10) Patent No.: US 8,587,779 B2
(45) Date of Patent: Nov. 19, 2013

(54) SPECTROMETER

(75) Inventors: Kazuya Iguchi, Hamamatsu (JP); Kengo Suzuki, Hamamatsu (JP)

(73) Assignee: Hamamatsu Photonics K.K., Hamamatsu-shi, Shizoka (JP)

( * ) Notice: Subject to any disclaimer, the term of this patent is extended or adjusted under 35 U.S.C. 154(b) by 37 days.

(21) Appl. No.: 13/126,523

(22) PCT Filed: Sep. 24, 2009

(86) PCT No.: PCT/JP2009/066526
§ 371 (c)(1),
(2), (4) Date: Apr. 28, 2011

(87) PCT Pub. No.: WO2010/073784
PCT Pub. Date: Jul. 1, 2010

(65) Prior Publication Data
US 2011/0205537 A1    Aug. 25, 2011

(30) Foreign Application Priority Data
Dec. 24, 2008  (JP) .................................. 2008-327845

(51) Int. Cl.
G01J 3/28    (2006.01)
(52) U.S. Cl.
USPC .......................................... 356/326; 356/445
(58) Field of Classification Search
USPC ................. 356/445, 446, 447, 448, 326, 319; 250/228, 372, 370.07, 459.1, 461.1
See application file for complete search history.

(56) References Cited

U.S. PATENT DOCUMENTS 3,874,799 A * 4/1975 Isaacs et al. .................. 356/402
4,572,668 A   2/1986 Auth
4,746,214 A * 5/1988 Akiyama et al. .............. 356/325
(Continued)

FOREIGN PATENT DOCUMENTS

CN    86106696    4/1987
GB    2181268     4/1987
(Continued)

OTHER PUBLICATIONS

Kazuhiko Koike et al., "A simple integrating-sphere fluorometer for monitoring the growth of benthic microalgae", La mer 32: 1994, p. 45-50, including English translation.

(Continued)

Primary Examiner — Sang Nguyen
(74) Attorney, Agent, or Firm — Drinker Biddle & Reath LLP

(57) ABSTRACT

A spectrometer 1A is provided with an integrating sphere 20 for observing measured light emitted from a sample S of a measurement target, and a Dewar vessel 50 which retains a medium R for regulating temperature of the sample S, so as to cover the sample S and a second container portion 50b of which is located so as to face the interior of the integrating sphere 20. The sample S can be easily regulated at a desired temperature with the use of the Dewar vessel 50 retaining the medium R so as to cover the sample S. As the second container portion 50b is located so as to face the interior of the integrating sphere 20, the temperature of the sample S is regulated by the medium R, while inhibiting an external ambience around the integrating sphere from affecting the sample S. Therefore, the sample S can be efficiently regulated at a desired temperature.

16 Claims, 14 Drawing Sheets

(56) References Cited

U.S. PATENT DOCUMENTS

| | | | |
|---|---|---|---|
| 4,990,782 A * | 2/1991 | Wellman et al. | 250/352 |
| 5,098,195 A | 3/1992 | Halyo et al. | |
| 5,258,363 A * | 11/1993 | Hed | 505/160 |
| 5,471,053 A * | 11/1995 | Diner et al. | 250/228 |
| 5,517,315 A * | 5/1996 | Snail et al. | 356/445 |
| 5,745,234 A * | 4/1998 | Snail et al. | 356/236 |
| 6,147,350 A * | 11/2000 | Beecroft et al. | 250/339.08 |
| 7,339,665 B2 * | 3/2008 | Imura | 356/243.1 |
| 7,508,503 B2 | 3/2009 | Jang | |
| 7,869,049 B2 * | 1/2011 | Baba et al. | 356/446 |
| 8,324,561 B2 | 12/2012 | Iguchi et al. | |
| 2008/0204705 A1 | 8/2008 | Liu | |

FOREIGN PATENT DOCUMENTS

| | | |
|---|---|---|
| JP | 54-35114 | 10/1979 |
| JP | 61-82442 | 4/1986 |
| JP | 2-236453 | 9/1990 |
| JP | 3-268443 | 11/1991 |
| JP | 6-201585 | 7/1994 |
| JP | 7-146175 | 6/1995 |
| JP | 11-173982 | 7/1999 |
| JP | 2001-059812 | 3/2001 |
| JP | 2003-215041 | 7/2003 |
| JP | 2005-140546 | 6/2005 |
| JP | 2007-33334 | 2/2007 |
| JP | 2007-86031 | 4/2007 |
| JP | 2007-198983 | 8/2007 |
| JP | 2009-31015 | 2/2009 |
| JP | 2009-31016 | 2/2009 |
| JP | 2009-74866 | 4/2009 |
| WO | WO 2007/007947 | 1/2007 |

OTHER PUBLICATIONS

M. Thiede et al., "In situ UV/Vis/near-IR diffuse reflection measurement of catalysts at temperatures up to 673 K", Review of Scientific Instruments, Feb. 2002, vol. 73, No. 2, p. 394-397.

G. Palmer et al., "Diffuse Reflectance Spectroscopy of Frozen Samples as an Adjunct to Low-Temperature Electron Paramagnetic Resonance Spectroscopy," Analytical Biochemistry, vol. 8, No. 1, May 1, 1964, pp. 95-103, XP024817418.

K. Klier et al., "Spectra of Zynthetic Zeolites Containing Transition Metal Ions-II. $Ni^{2+}$ IONS in Type A Linde Molecular Sieves," Journal of Physics and Chemistry of Solids, vol. 29, No. 6, Jun. 1, 1968, pp. 951-957, XP024582194.

W. Chung-Chih et al., "Hole-Transport Properties of a Furan-Containing Oligoaryl," Journal of Applied Physics, vol. 93, No. 9, May 1, 2003, pp. 5465-5471, XP012059556.

L. S. Slobodkin et al., "Near Infrared Reflection Spectra of Ammonia Frost: Interpretation of the Upper Clouds of Saturn," Journal of Quantitative Spectroscopy and Radiative Transfer, vol. 20, No. 5, Nov. 1, 1978, pp. 481-490, XP024424975.

E.J. Bowen et al., "The Effect of Temperature on Fluorescence of Solutions," J. Phys. Chem., vol. 63 (1), Jan. 1959, pp. 4-7.

* cited by examiner

SPECTROMETER

TECHNICAL FIELD

The present invention relates to a spectrometer provided with an integrating sphere and adapted for measuring a sample regulated at a desired temperature.

BACKGROUND ART

There is a known spectrometer which is provided with an integrating sphere for observing measured light emitted from a sample and which is configured to cool the sample (e.g., cf. Patent Literature 1). In the spectrometer described in Patent Literature 1, the sample is cooled at a desired temperature by bringing the sample, which is arranged to face the interior of the integrating sphere, into contact with a refrigerant.

There is another known spectrometer provided with an integrating sphere and adapted for cooling the interior of the integrating sphere (e.g., cf. Patent Literature 2). In the spectrometer described in Patent Literature 2, cold air is introduced into the integrating sphere to cool the integrating sphere at a desired temperature.

Applicants filed applications entitled a light detecting apparatus provided with an integrating sphere (e.g., cf. Patent Literature 3).

CITATION LIST

Patent Literature

Patent Literature 1: Japanese Patent Application Laid-open No. S61-082442
Patent Literature 2: Japanese Patent Application Laid-open No. H07-146175
Patent Literature 3: Japanese Patent Application Laid-open No. 2007-86031

SUMMARY OF INVENTION

Technical Problem

In the spectrometer described in Patent Literature 1, the sample is cooled by bringing the sample into contact with the refrigerant, but the temperature of the sample is affected by an external ambience because the sample is located outside the integrating sphere. For this reason, it was difficult to easily and efficiently regulate the sample at a desired temperature.

In the spectrometer described in Patent Literature 2, cold air is introduced into the integrating sphere to cool the integrating sphere, which is for absorbing heat generated from a lamp disposed in the integrating sphere, and nothing is considered about cooling of the sample to regulate the temperature.

It is an object of the present invention to provide a spectrometer capable of easily and efficiently regulating a sample at a desired temperature.

Solution to Problem

The present invention is characterized by comprising: an integrating sphere for observing measured light emitted from a sample of a measurement target: and a Dewar vessel which retains a medium for regulating temperature of the sample, so as to cover the sample and at least a portion of which is located so as to face the interior of the integrating sphere.

In the present invention, the sample can be easily regulated at a desired temperature with the use of the Dewar vessel which retains the medium for regulating the temperature of the sample, so as to cover the sample. Furthermore, in the present invention, at least a portion of the Dewar vessel is located so as to face the interior of the integrating sphere. For this reason, the temperature of the sample can be regulated by the medium, while inhibiting an external ambience around the integrating sphere from affecting the sample. Therefore, the sample can be efficiently regulated at a desired temperature.

Incidentally, the applicants found that in the configuration wherein the Dewar vessel was arranged so that at least a portion thereof faced the interior of the integrating sphere, when excitation light directly irradiated the sample in the Dewar vessel and measured light emitted from the sample was measured, a quantum yield intrinsic to the sample was not obtained in some cases. The applicants conducted further research and discovered that the cause was leakages of the excitation light and the measured light through a Dewar insertion opening of the integrating sphere. The applicants also discovered that the measured light leaked more than the excitation light through the Dewar insertion opening. A conceivable reason for it is that since the sample is disposed in the Dewar vessel, the measured light emitted from the sample is refracted by at least the portion of the Dewar vessel mentioned above and part of the measure light leaks through the Dewar insertion opening to the outside of the integrating sphere.

For example, in quantum yield measurement, a quantum yield is determined by a rate of a light intensity of the excitation light absorbed by the sample and a light intensity of the measured light emitted from the sample. For this reason, the measurement accuracy of quantum yield may degrade if there is a difference between rates of leaking light quantities of the excitation light and the measured light to the outside of the integrating sphere. Then the applicants found that the foregoing problem was solved by the configuration described below.

The present invention is preferably embodied in the configuration further comprising: irradiation light supplying means which supplies excitation light into the integrating sphere; diffusely reflecting means which diffusely reflects the excitation light, as irradiated with the excitation light in the integrating sphere; and a sample holder which has a portion holding the sample and which is disposed inside the Dewar vessel so as to locate the portion holding the sample in the integrating sphere, wherein the integrating sphere has an entrance aperture for inputting the excitation light thereinto, and wherein the portion of the sample holder holding the sample is disposed away from an optical path of the excitation light between the entrance aperture and the diffusely reflecting means and is irradiated with the excitation light diffusely reflected by the diffusely reflecting means. In this case, the excitation light diffusely reflected by the diffusely reflecting means irradiates the portion of the sample holder holding the sample, thereby to reduce the light intensity of the excitation light to irradiate the sample. This leads to reduction in light intensity of the measured light emitted from the sample, so as to reduce the rate of light intensity of the measured light leaking to the exterior of the integrating sphere. Therefore, it decreases the difference between rates of light quantities of the excitation light and the measured light leaking to the exterior of the integrating sphere, which can suppress the degradation of measurement accuracy of quantum yield.

More preferably, the diffusely reflecting means is an internal surface of the integrating sphere. In this case, the excitation light can be diffusely reflected without provision of a separate diffusely reflecting means except for the integrating sphere.

More preferably, at least a portion of the Dewar vessel is disposed away from the optical path. In this case, it is feasible to inhibit the excitation light from being absorbed by at least the portion of the Dewar vessel mentioned above or from being refracted to leak to the exterior of the integrating sphere, in the optical path of the excitation light between the entrance aperture and the diffusely reflecting means. Therefore, the degradation of measurement accuracy of quantum yield can be further suppressed.

Preferably, the diffusely reflecting means is a diffuser plate which is arranged between the portion of the sample holder holding the sample and the entrance aperture and which diffusely reflects the excitation light. In this case, the excitation light can be easily diffusely reflected.

Advantageous Effects of Invention

The present invention provides the spectrometer capable of easily and efficiently regulating the sample at a desired temperature.

DESCRIPTION OF EMBODIMENTS

Preferred embodiments of the present invention will be described below in detail with reference to the accompanying drawings. In the description, the same elements or elements with the same functionality will be denoted by the same reference signs, without redundant description.

Figure 1:
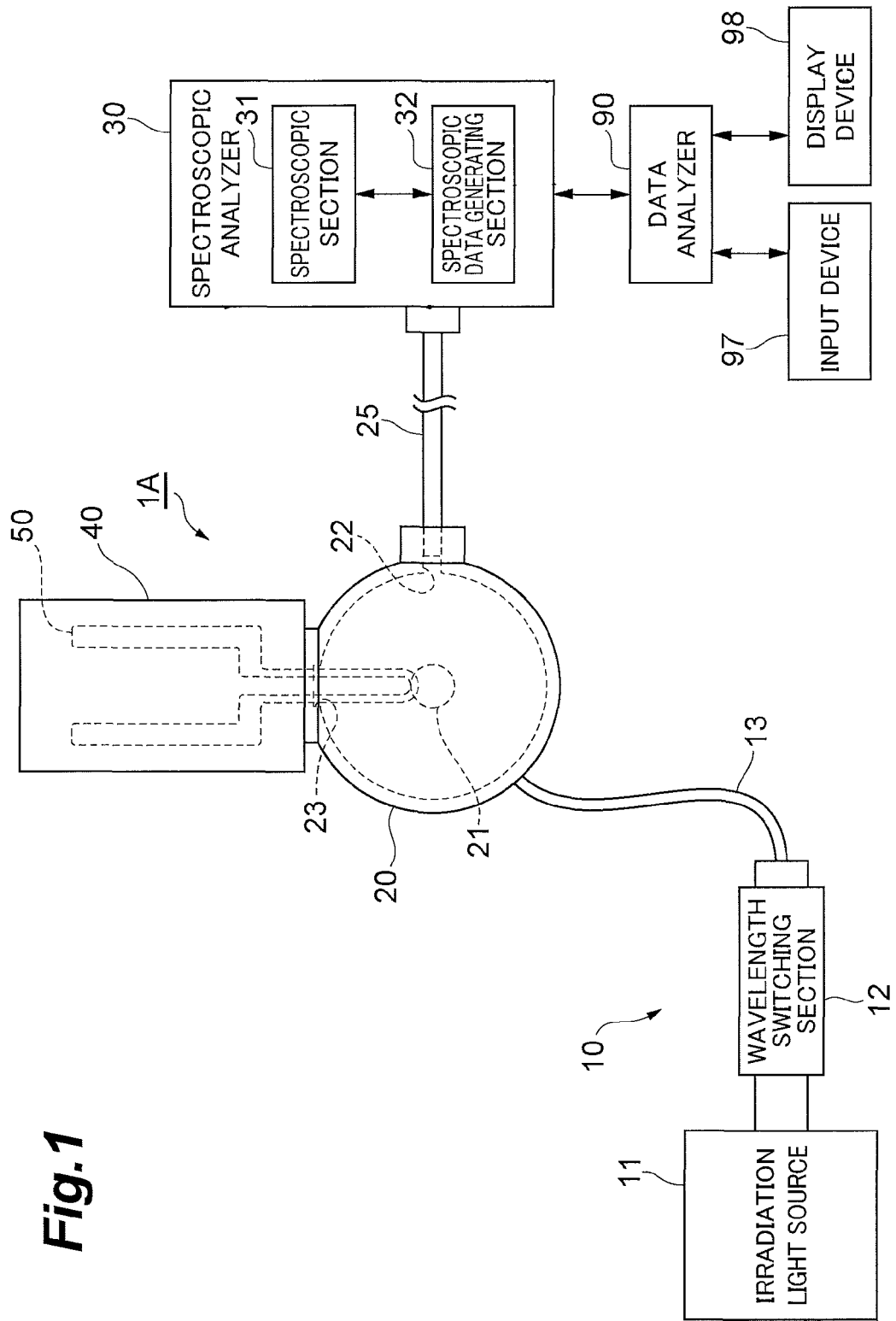
FIG. 1 is a drawing schematically showing a configuration of an embodiment of the spectrometer.

FIG. 1 is a drawing schematically showing a configuration of a spectrometer according to an embodiment of the present invention. The spectrometer 1A of the present embodiment is provided with an irradiation light supplying section 10, an integrating sphere 20, a spectroscopic analyzer 30, a Dewar housing 40, a Dewar vessel 50, and a data analyzer 90. The spectrometer 1A is configured as a quantum yield measuring apparatus which is able to irradiate a sample S such as a luminescence material with excitation light of a predetermined wavelength and to perform measurement and evaluation of luminescence properties such as a fluorescence property of the sample S by the photoluminescence (PL) method.

The irradiation light supplying section 10 supplies the excitation light for measurement of the luminescence properties of the sample S, as irradiation light supplied into the interior of the integrating sphere 20 housing the sample S of a measurement target. The irradiation light supplying section 10 functions as an irradiation light supplying means. In FIG. 1, the irradiation light supplying section 10 is composed of an irradiation light source 11, and a light guide 13 which guides the light from the irradiation light source 11 to the integrating sphere 20. In the irradiation light supplying section 10, a wavelength switching section 12 is set up between the irradiation light source 11 and the light guide 13. In this setup, the irradiation light supplying section 10 is configured to enable switch between the excitation light of the predetermined wavelength and light consisting of light components in a predetermined wavelength range (which will be referred to as white light). Therefore, the irradiation light supplying section 10 functions as an excitation light supplying means and white light supplying means.

A specific configuration example of the irradiation light supplying section 10 applicable herein is a configuration using a white light source as the irradiation light source 11 and providing the wavelength switching section 12 with a wavelength selection means to select only a light component in the predetermined wavelength range out of the light supplied from the irradiation light source 11 and to let the light component pass through the light guide 13. In this case, when the wavelength switching section 12 turns wavelength selection OFF, the irradiation light into the integrating sphere 20 is white light; when the wavelength switching section 12 turns wavelength selection ON, the irradiation light into the integrating sphere 20 is the excitation light of the predetermined wavelength. Specifically, the wavelength selection means applicable herein is, for example, a spectroscopic filter, a spectroscope, or the like.

The integrating sphere 20 is used in measurement of the luminescence properties of the sample S disposed inside. The integrating sphere 20 is configured with an entrance aperture 21 for inputting the excitation light with which the sample S is irradiated into the integrating sphere 20, an exit aperture 22 for outputting measured light from the sample S to the outside, and a first sample introduction opening 23 for introducing the sample S into the interior of the integrating sphere 20. The Dewar housing 40 is detachably fitted in the first sample introduction opening 23 with attachment screws.

An exit end of the light guide 13 for inputting of irradiation light is fixed to the entrance aperture 21 of the integrating sphere 20. The light guide 13 applicable herein is, for example, an optical fiber. An entrance end of a light guide 25 for guiding the measured light from the sample S to the latter-stage spectroscopic analyzer 30 is fixed to the exit aperture 22 of the integrating sphere 20. The light guide 25 applicable herein is, for example, a single fiber or a bundle fiber.

The spectroscopic analyzer 30 disperses the measured light from the sample S output from the exit aperture 22 of the integrating sphere 20 through the light guide 25, to obtain a wavelength spectrum thereof. The spectroscopic analyzer 30 functions as a dispersing means. In the present configuration example, the spectroscopic analyzer 30 is configured as a photonic multichannel analyzer having a spectroscopic section 31 and a spectroscopic data generating section 32.

The spectroscopic section 31 is composed of a spectrometer for resolving the measured light into wavelength components, and a photodetector for detecting light from the spectrometer. The photodetector applicable herein is, for example, a CCD linear sensor consisting of a one-dimensional array of pixels of multiple channels (e.g., 1024 channels) for detecting respective spectrally-resolved wavelength components of the measured light. A measured wavelength region by the spectroscopic section 31 may be optionally set according to a specific configuration and others and is, for example, from 200 nm to 950 nm. The spectroscopic data generating section 32 performs required signal processing for detection signals output from the respective channels of the photodetector of the spectroscopic section 31, to generate data of a wavelength spectrum being spectroscopic data of the measured light. The spectroscopic data generating section 32 functions as a spectroscopic data generating means. The data of the wavelength spectrum generated and obtained by the spectroscopic data generating section 32 is output to the latter-stage data analyzer 90.

The data analyzer 90 is a data analyzing means which performs a data analysis necessary for the wavelength spectrum obtained by the spectroscopic analyzer 30, to obtain information about the sample S. The specific content of the data analysis in the data analyzer 90 will be described later. Connected to the data analyzer 90 are an input device 97 used for input of instructions about the data analysis and others, input of analysis conditions, and so on, and a display device 98 used for display of the data analysis result and others.

Figure 2:
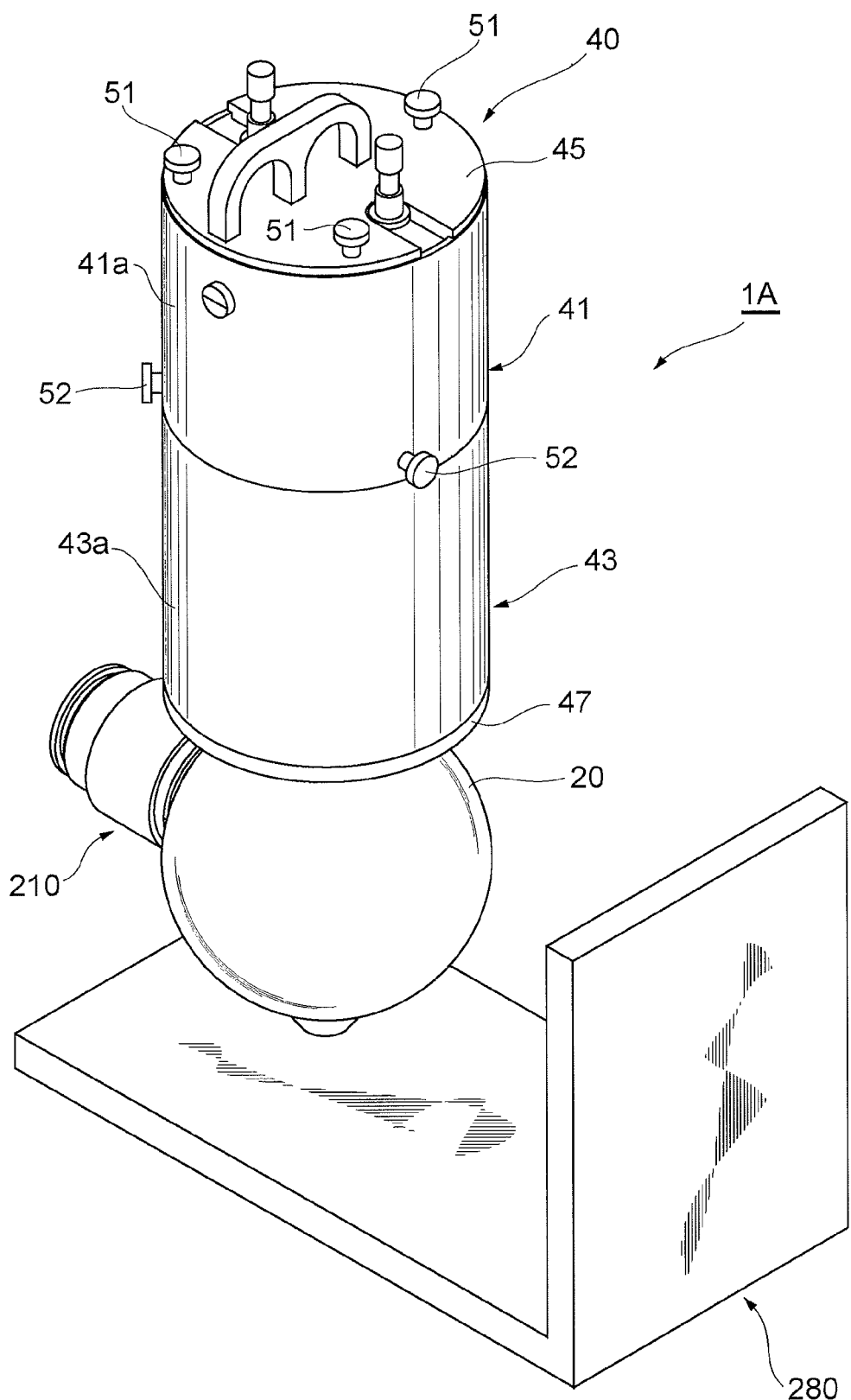
FIG. 2 is a perspective view showing an example of configurations of an integrating sphere and a Dewar housing.
Figure 3:
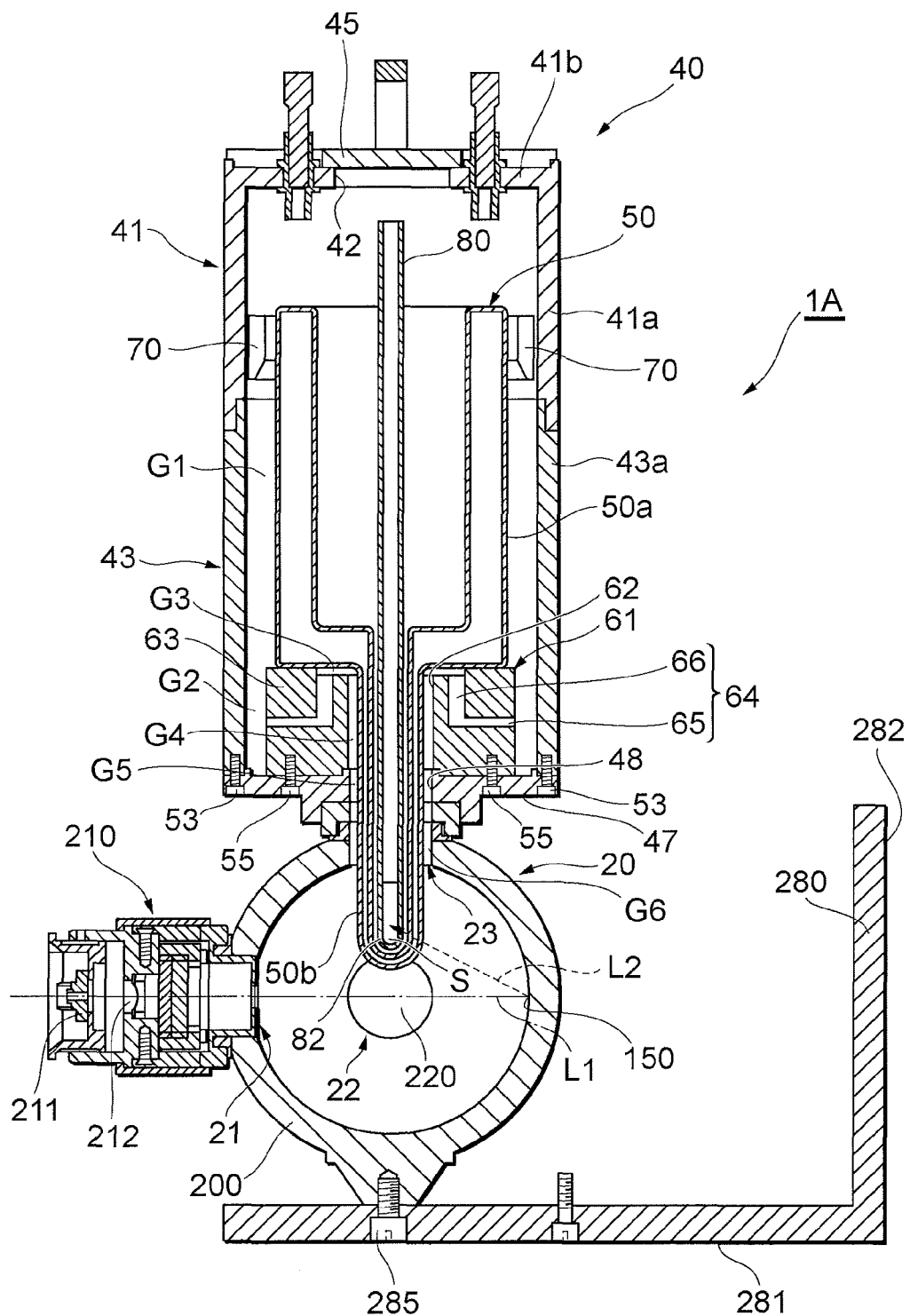
FIG. 3 is a sectional view showing an example of configurations of the integrating sphere, Dewar housing, and Dewar vessel.
Figure 4:
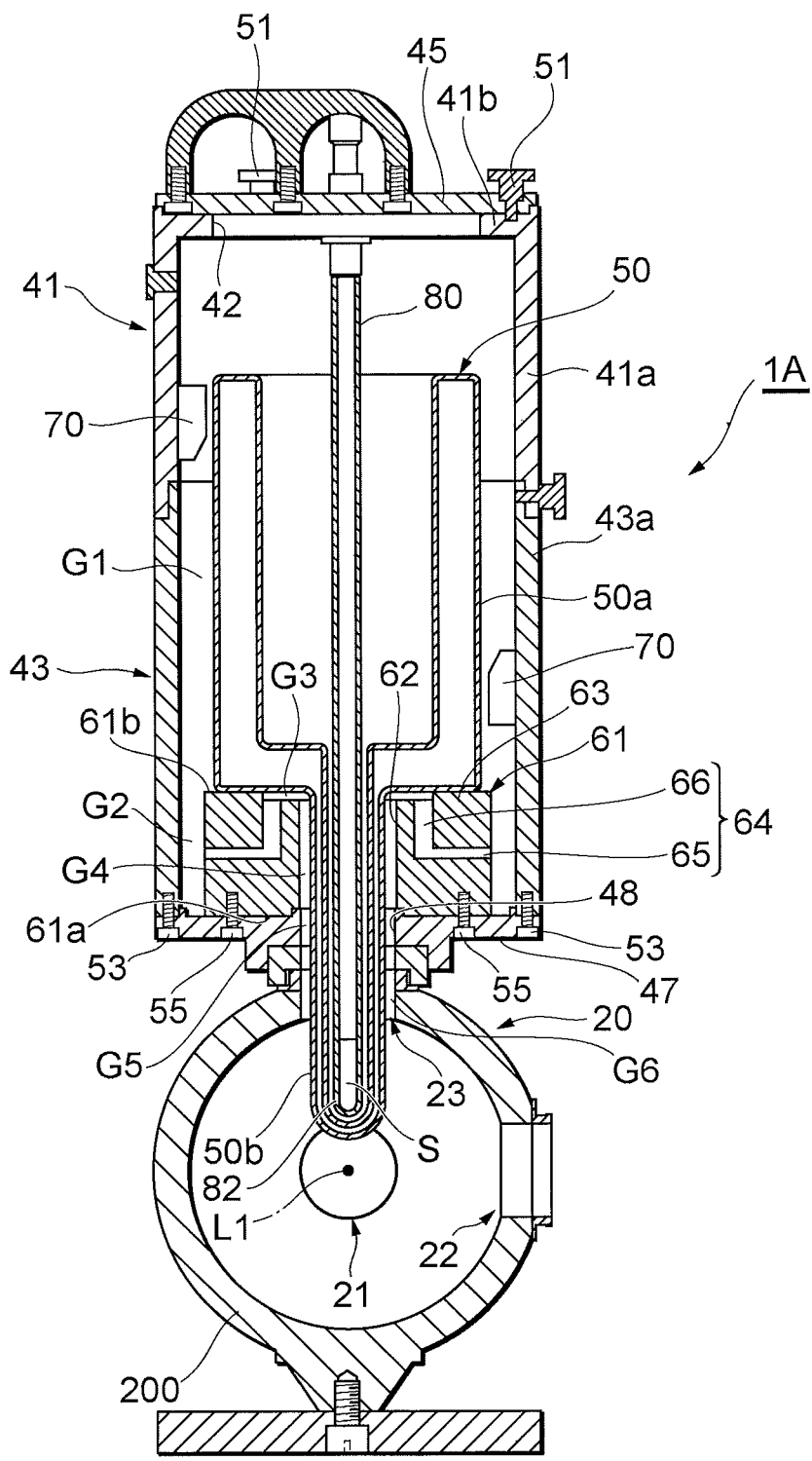
FIG. 4 is a sectional view showing an example of configurations of the integrating sphere, Dewar housing, and Dewar vessel.
Figure 5:
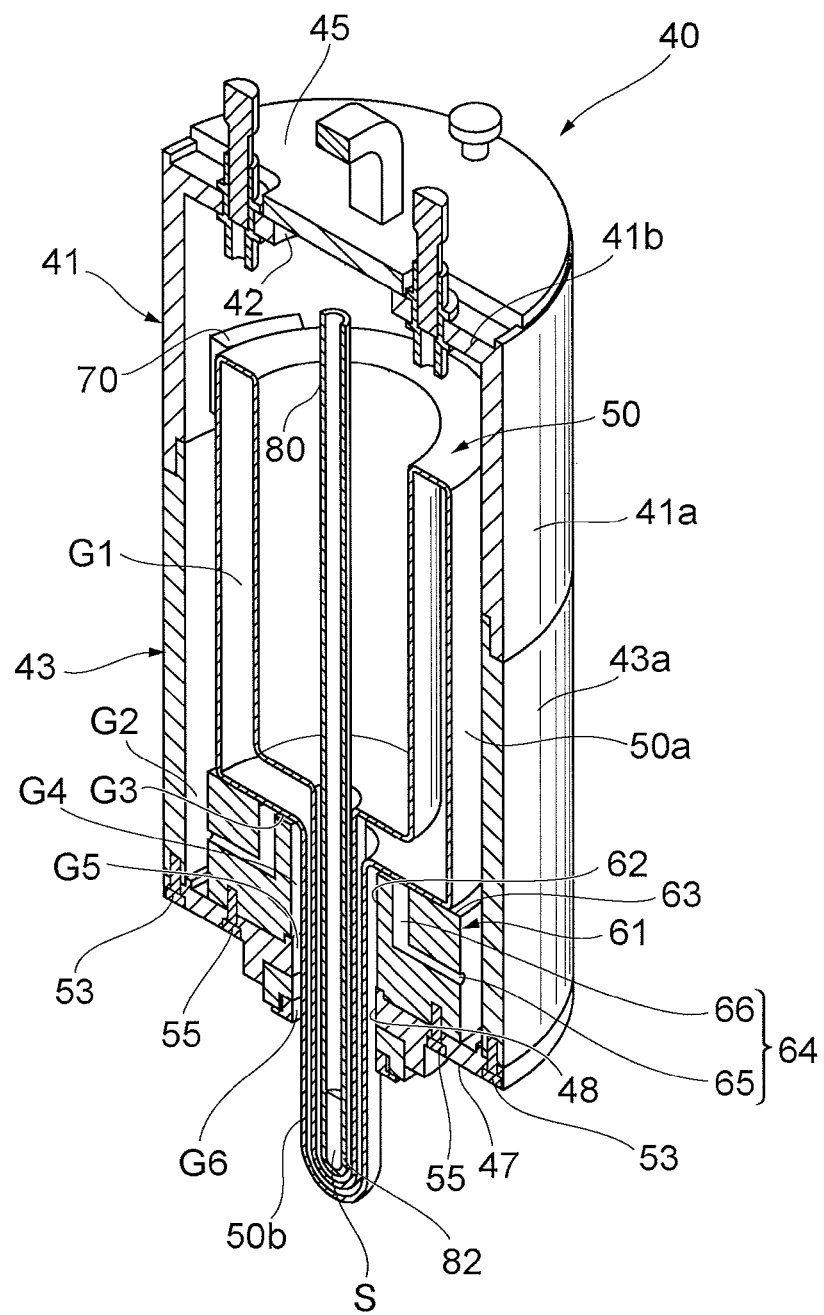
FIG. 5 is a sectional view showing an example of configurations of the integrating sphere, Dewar housing, and Dewar vessel.
Figure 6:
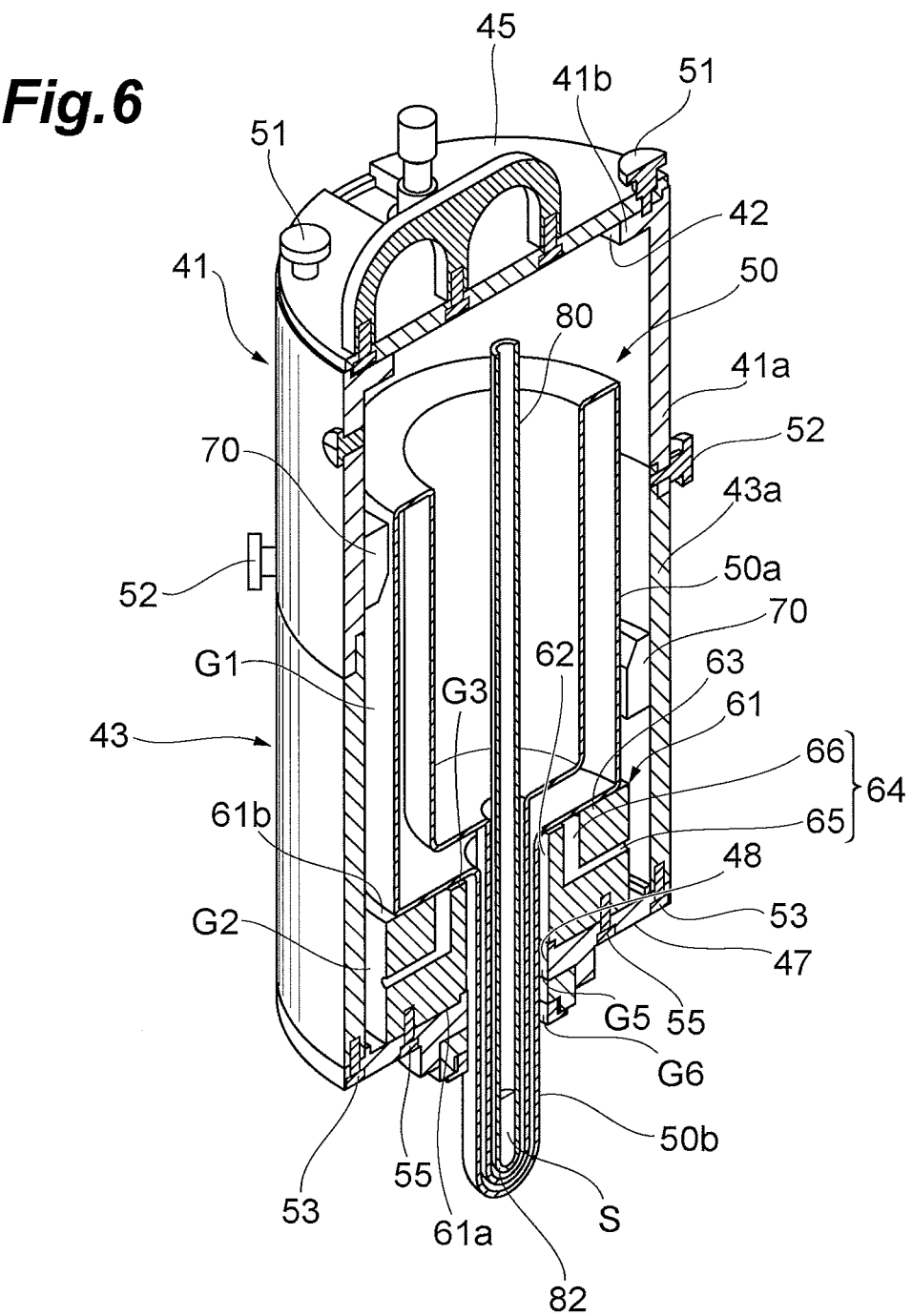
FIG. 6 is a sectional view showing an example of configurations of the integrating sphere, Dewar housing, and Dewar vessel.

The following will describe configurations of the integrating sphere 20, Dewar housing 40, and Dewar vessel 50 used in the spectrometer 1A shown in FIG. 1, with reference to FIGS. 2 to 6. FIG. 2 is a perspective view showing an example of the configurations of the integrating sphere 20 and Dewar housing 40 used in the spectrometer 1A shown in FIG. 1. FIGS. 3 to 6 are sectional views showing an example of the configurations of the integrating sphere 20, Dewar housing 40, and Dewar vessel 50 and show the configurations of the integrating sphere 20, Dewar housing 40, and Dewar vessel 50 in cross sections along the optical path L1 of the excitation light. The cross sections in FIGS. 3 and 5 and the cross sections in FIGS. 4 and 6 are perpendicular to each other.

The integrating sphere 20 is provided with an integrating sphere body 200 attached to a mount 280 with an attachment screw 285. The mount 280 is formed in an L-shape with two ground contact surfaces 281, 282 perpendicular to each other. The optical path L1 extends in a direction parallel to the ground contact surface 281 and perpendicular to the ground contact surface 282, while passing the center position of the integrating sphere body. 200.

The integrating sphere body 200 is provided with the entrance aperture 21, exit aperture 22, and first sample introduction opening 23 shown in FIG. 1. The entrance aperture 21 is provided at a predetermined position of the integrating sphere body 200 on one end side of the optical path L1 (i.e., at a left position in the drawing). The exit aperture 22 is provided at a predetermined position on a surface passing the center position of the integrating sphere body 200 and being perpendicular to the optical path L1. The first sample introduction opening 23 is provided at a position of a 90° shift (upper position in the drawing) from the exit aperture 22 when viewed from the center position on the surface passing the center position of the integrating sphere body 200 and being perpendicular to the optical path L1.

A light guide holder 210 for connection of the light guide 13 for inputting of irradiation light is inserted and fitted in the entrance aperture 21. A light guide holder 220 for connection of the light guide 25 for outputting of measured light is inserted and fitted in the exit aperture 22. FIGS. 2 to 6 are drawn without illustration of the light guides 13, 25.

Provided in the Dewar housing 40 are a sample holder 80 which holds the sample S at a predetermined position in the integrating sphere 20, and the Dewar vessel 50 for regulating the temperature of the sample S held in the sample holder 80. The sample holder 80 is a tubular member closed at one end and has a sample holding portion 82 which holds the sample S, at one end. The Dewar vessel 50 is for retaining a medium for regulating the temperature of the sample S (e.g., a refrigerant such as liquid nitrogen, or a heat medium such as water) and is a nearly tubular container closed at one end. The Dewar vessel 50 is constructed in a heat-insulated double structure with a vacuum layer. The sample holder 80 is arranged as positioned inside the Dewar vessel 50. The Dewar vessel 50 has a first container portion 50a having a first inside diameter and located on the other end side, and a second container portion 50b having a second inside diameter smaller than the first inside diameter and located on one end side.

The second inside diameter is set larger than the outside diameter of the sample holder 80 and, in a state in which the sample holder 80 is disposed in the Dewar vessel 50, a space is created between the second container portion 50b and the sample holder 80. The medium for regulating the temperature is retained in the space between the second container portion 50b and the sample holder 80. The sample S held in the sample holding portion 82 is covered by the medium through the sample holder 80, whereby the temperature thereof is regulated.

The Dewar housing 40 is a member having a space for housing the Dewar vessel 50 inside, and has a first case 41, a second case 43, a first lid plate 45, and a second lid plate 47. The first case 41 consists of a cylinder portion 41a of a tubular shape (cylindrical shape in the present embodiment) and a bottom portion 41b located on one end side of the cylinder portion 41a, and is a member with a bottom. The bottom portion 41b has an opening 42 formed in a central region thereof. The first lid plate 45 is detachably attached to the bottom portion 41b of the first case 41 with attachment screws 51, to close the opening 42 formed in the bottom portion 41b.

The second case 43 consists of a cylinder portion 43a of a tubular shape (cylindrical shape in the present embodiment) opening at both ends. The first case 41 and second case 43 are detachably attached to each other with attachment screws 52 and fixed in a state in which their respective other ends are in contact with each other. The second lid plate 47 is detachably attached to one end of the second case 43 with attachment screws 53 to close an opening at the one end. An opening 48 for insertion of the second container portion 50b of the Dewar vessel 50 is formed in a central region of the second lid plate 47 so as to communicate with the first sample introduction opening 23.

The Dewar vessel 50 is radially positioned by a plurality of spacers 70 disposed at predetermined intervals on internal peripheral surfaces of the first case 41 and the second case 43. The spacers 70 form a predetermined gap G1 between the internal peripheral surfaces of the first case 41 and the second case 43 and the external peripheral surface of the first container portion 50a of the Dewar vessel 50.

A support pedestal 61 supporting the Dewar vessel 50 is detachably attached to the second lid plate 47 with attachment screws 55. The support pedestal 61 is a nearly columnar member and a through hole 62 for insertion of the second container portion 50b of the Dewar vessel 50 is formed in a central portion of the support pedestal 61 so as to communicate with the opening 48 formed in the second lid plate 47. A predetermined gap G2 is formed between the internal peripheral surface of the second case 43 and the external peripheral surface of the support pedestal 61. An annular packing (not shown) is provided so as to surround the through hole 62, between the second lid plate 47 and the support pedestal 61. As this packing is interposed between the second lid plate 47 and the support pedestal 61, water-tightness is achieved between the second lid plate 47 and the support pedestal 61.

The support pedestal 61 is provided with a projecting portion 63 projecting from a second surface 61b, on the second surface 61b opposed to a first surface 61a attached to the second lid plate 47. The projecting portion 63 is formed in a ring shape, when viewed from the center axis direction of the through hole 62, so as to surround the outside of the through hole 62. The projecting portion 63 is in contact with the Dewar vessel 50 to define the position of the Dewar vessel 50 in an insertion direction thereof. The second surface 61b of the support pedestal 61 and the Dewar vessel 50 are separated by a distance of a height of the projecting portion 63 to form a predetermined gap G3 between the second surface 61b of the support pedestal 61 and the Dewar vessel 50. An annular packing (not shown) is provided so as to surround the projecting portion 63, between the support pedestal 61 and the Dewar vessel 50. As this packing is interposed between the support pedestal 61 and the Dewar vessel 50, water-tightness is achieved between the support pedestal 61 and the Dewar vessel 50.

The support pedestal 61 is provided with a plurality of communicating passages 64 which are formed so as to establish communication between the predetermined gap G2 formed between the internal peripheral surface of the second case 43 and the external peripheral surface of the support pedestal 61, and the predetermined gap G3 formed between the second surface 61b of the support pedestal 61 and the Dewar vessel 50. The communicating passages 64 are arranged at equiangular intervals (e.g., at intervals of approximately 90° around the center axis of the through hole 62. Each communicating passage 64 consists of a first passage portion 65 and a second passage portion 66. The first passage portion 65 opens on the external peripheral surface of the support pedestal 61 and extends in a radial direction of the support pedestal 61 from the external peripheral surface of the support pedestal 61. The second passage portion 66 extends in a direction parallel to the center axis of the through hole 62 from the first passage portion 65 and opens on the second surface 61b.

Predetermined gaps G4, G5, and G6 are formed between the external periphery of the second container portion 50b of the Dewar vessel 50 and the internal peripheral surface of the through hole 62 formed in the support pedestal 61, between the external periphery of the second container portion 50b and the internal peripheral surface of the opening 48 formed in the second lid plate 47, and between the external periphery of the second container portion 50b and the internal peripheral surface of the first sample introduction opening 23, respectively. The gaps G4, G5, and G6 communicate with each other and also communicate with the predetermined gap G3 between the second surface 61b of the support pedestal 61 and the Dewar vessel 50 and with the space in the integrating sphere 20. These cause the space in the Dewar vessel 50 to communicate with the space in the integrating sphere 20 through the plurality of communicating passages 64 formed in the support pedestal 61, the predetermined gap G3 formed between the second surface 61b of the support pedestal 61 and the Dewar vessel 50, the predetermined gap G4 formed between the external periphery of the second container portion 50b and the internal peripheral surface of the through hole 62, the predetermined gap G5 formed between the external periphery of the second container portion 50b and the internal peripheral surface of the opening 48 of the second lid plate 47, and the predetermined gap G6 formed between the external periphery of the second container portion 50b and the internal peripheral surface of the first sample introduction opening 23.

The length of the second container portion 50b is so set that the tip portion of the second container portion 50b projects by a predetermined length into the integrating sphere 20 in a state in which the Dewar vessel 50 is in contact with a contact surface of the support pedestal 61. Particularly, the length of the second container portion 50b is set so that the tip portion of the second container portion 50b is located between the center position of the integrating sphere body 200 and the first sample introduction opening 23. Inside the second container portion 50b, the sample holding portion 82 is arranged so as to be located in the integrating sphere 20. This makes the sample holding portion 82 and the sample S located between the center position of the integrating sphere body 200 and the first sample introduction opening 23.

The Dewar vessel 50 and the sample holder 80 are preferably made of a material that transmits light including the excitation light and the measured light, and a material suitably applicable herein is, for example, an optical cell made of synthetic silica glass.

The first sample introduction opening 23 and the sample holder 80 can be suitably used, for example, in the case where the sample S is a solution with a luminescence material being dissolved therein. This sample holder 80 can also be used where the sample S is a solid sample, a powder sample, or the like. When the sample holder 80 is used, the integrating sphere 20 is set in a state in which the ground contact surface 281 of the mount 280 faces down so that a line connecting the entrance opening 21 and the center position of the integrating sphere body 200 extends along a horizontal line.

The light guide 13 for inputting of irradiation light is held in a state in which it is positioned by a light guide holding portion 211 of the light guide holder 210. The light from the irradiation light source 11 (cf. FIG. 1) is guided to the integrating sphere 20 by the light guide 13 and, while being collected by a condensing lens 212 in the light guide holder 210, it is radiated into the integrating sphere 20. In the present embodiment, the second container portion 50b, the sample holding portion 82, and the sample S are located at the position away from the optical path L1 of the excitation light between the entrance aperture 21 and an internal surface 150 at the position opposite to the entrance aperture 21 (i.e., at the right position in the drawing). The light guide 25 for outputting of measured light is held in a state in which it is positioned by the light guide holder 220.

When the excitation light of the predetermined wavelength as irradiation light from the irradiation light supplying section 10 is supplied from the entrance aperture 21, the excitation light travels along the optical path L1 to irradiate the internal surface 150. The excitation light impinging on the internal surface 150 is multiply diffusely reflected by the high diffuse reflection powder (e.g., Spectralon (registered trademark), barium sulfate, or the like) applied over the internal surface of the integrating sphere body 200. The diffusely reflected light travels along an optical path L2 to irradiate the sample holding portion 82 and the sample S, whereupon the sample S emits measured light. The measured light emitted from the sample S passes through the second container portion 50b and the sample holding portion 82 and thereafter it enters the light guide 25 connected to the light guide holder 220 to be guided as measured light to the spectroscopic analyzer 30. This leads to execution of spectrometry of the measured light from the sample S. The light from the sample S to be the measured light includes luminescence such as fluorescence produced in the sample S by irradiation with the excitation light, and the light component resulting from scattering, reflection, etc. of the excitation light by the sample S.

Figure 7:
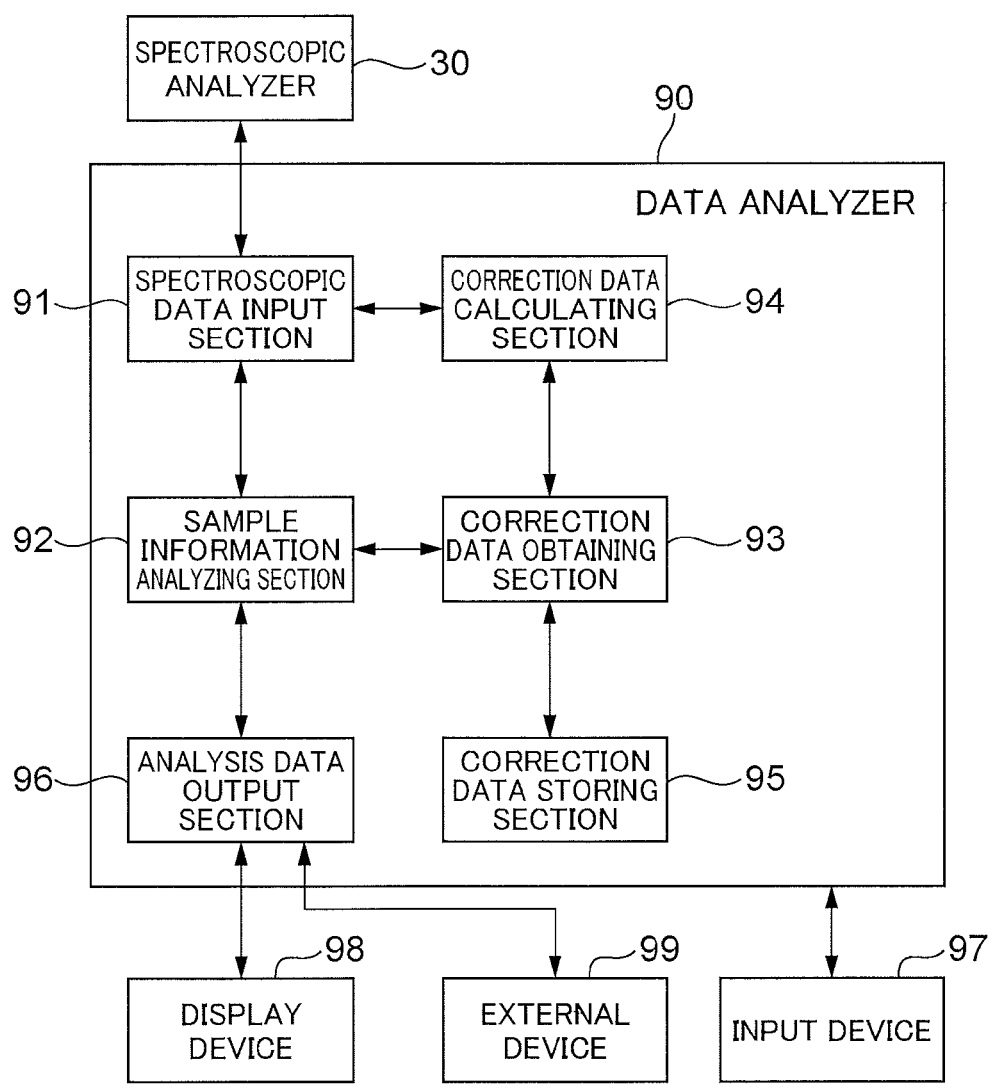
FIG. 7 is a block diagram showing an example of a configuration of a data analyzer.

FIG. 7 is a block diagram showing an example of the configuration of the data analyzer 90 used in the spectrometer 1A shown in FIG. 1. The data analyzer 90 in the present configuration example is configured with a spectroscopic data input section 91, a sample information analyzing section 92, a correction data obtaining section 93, and an analysis data output section 96. The data analyzer 90 is provided with a correction data calculating section 94 and a correction data storing section 95 in association with the correction data obtaining section 93.

The spectroscopic data input section 91 receives input of data such as a wavelength spectrum obtained as spectroscopic data by the spectroscopic analyzer 30. The spectroscopic data input section 91 functions as an input means. The spectroscopic data input through the spectroscopic data input section 91 is sent to the sample information analyzing section 92. The sample information analyzing section 92 analyzes the input wavelength spectrum to obtain information about the sample S. The sample information analyzing section 92 functions as a sample information analyzing means. The correction data obtaining section 93 obtains correction data for correction for the wavelength spectrum in view of light absorption by the sample holder 80, specifically, absorption of at least either the excitation light or the measured light emitted from the sample S, for the aforementioned configuration wherein the sample S is held in the sample holder 80 in the integrating sphere 20. The correction data obtaining section 93 functions as a correction data obtaining means. The sample information analyzing section 92 corrects the wavelength spectrum with the correction data obtained by the correction data obtaining section 93 and analyzes the corrected wavelength spectrum to obtain information of the sample S such as a luminescence quantum yield by the PL method.

The correction data for the wavelength spectrum can be obtained, for example, from the correction data calculating section 94. The correction data calculating section 94 refers to the wavelength spectrum of the measurement result for derivation of the correction data executed under a predetermined condition and calculates the correction data, based thereon. The correction data calculating section 94 functions as a correction data calculating means. A specific calculation method of the correction data will be described below. If the correction data for the wavelength spectrum is preliminarily obtained, it is also possible to adopt a configuration wherein the correction data is stored in the correction data storing section 95 and wherein the correction data obtaining section 93 reads and obtains the correction data therefrom as occasion demands. In this case, the data analyzer may be configured without the correction data calculating section 94. The data analyzer may also employ a configuration wherein the correction data calculated by the correction data calculating section 94 is stored in the correction data storing section 95 and wherein the correction data obtaining section 93 reads the correction data as occasion demands.

The analysis data output section 96 outputs the analysis result of sample information resulting from the analysis by the sample information analyzing section 92. The analysis data output section 96 functions as an output means. When the data of the analysis result is fed to the display device 98 through the analysis data output section 96, the display device 98 displays the analysis result on a predetermined display screen for an operator. The recipient to receive the output of the analysis result is not always limited solely to the display device 98, but the data may be output to another device. FIG. 7 shows the configuration wherein an external device 99, in addition to the display device 98, is connected to the analysis data output section 96. Examples of the external device 99 include a printer, an external memory, other terminal equipment, and so on.

The spectrometer 1A shown in FIGS. 1 to 6 is provided with the integrating sphere 20 provided with the entrance aperture 21 for inputting of excitation light and the exit aperture 22 for outputting of measured light and configured to enable the measurement of the luminescence properties of the sample S by the PL method, and the spectroscopic analyzer 30 which spectroscopically measures light so as to allow distinguishment between the excitation light and the measured light from the sample S by their wavelength spectra. For the sample holder 80 holding the sample S in the integrating sphere 20, the data analyzer 90 prepares the correction data taking account of light absorption by the sample container, corrects the wavelength spectrum with this correction data, and then performs the analysis of the wavelength spectrum and the derivation of the sample information. This enables the spectrometry of the sample S to be suitably and accurately carried out, while suppressing error in the analysis result such as the luminescence quantum yield, even in the case where influence of light absorption by the sample holder 80 is unignorable.

Figure 8:
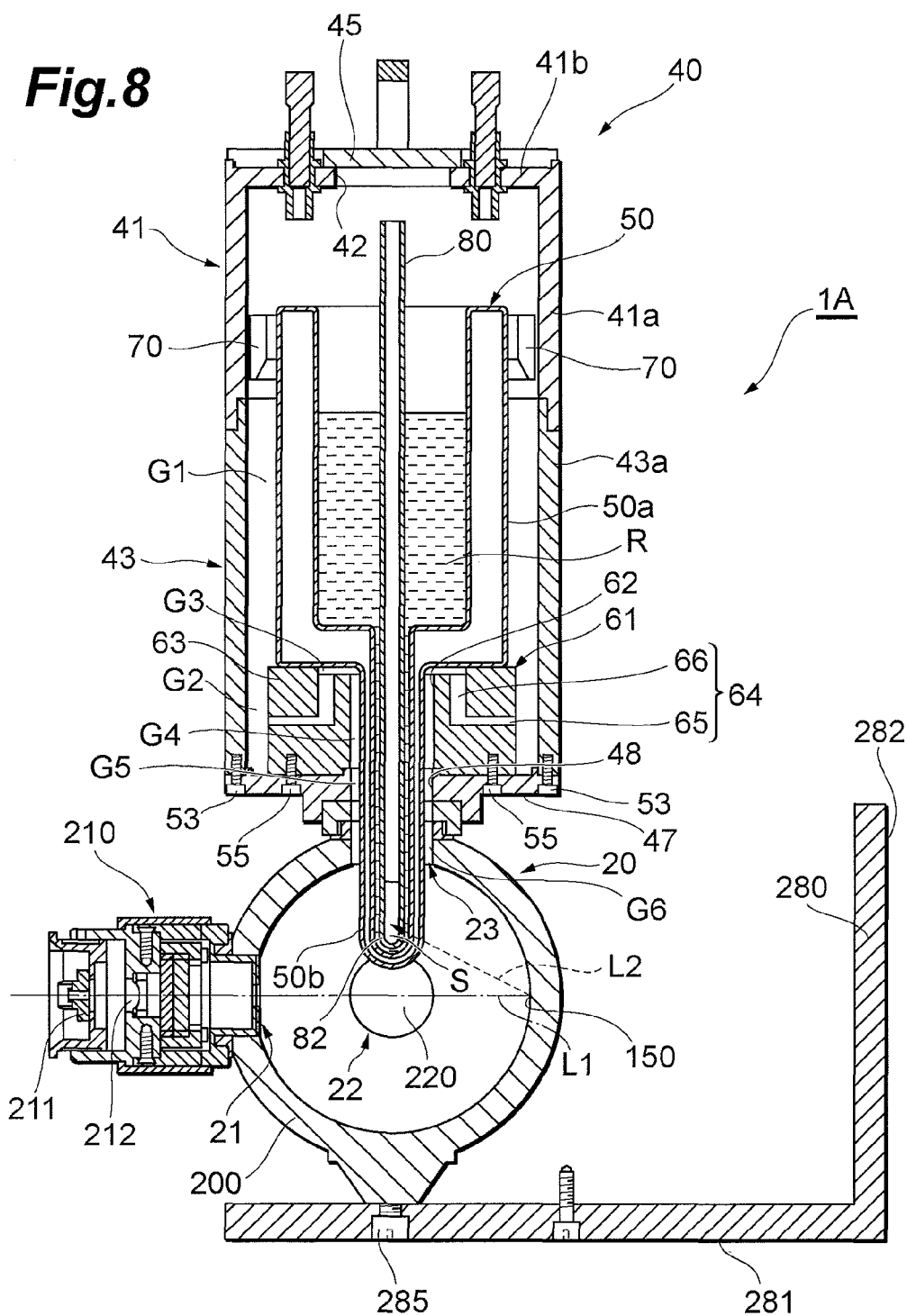
FIG. 8 is a sectional view showing an example of configurations of the integrating sphere, Dewar housing, and Dewar vessel.
Figure 9:
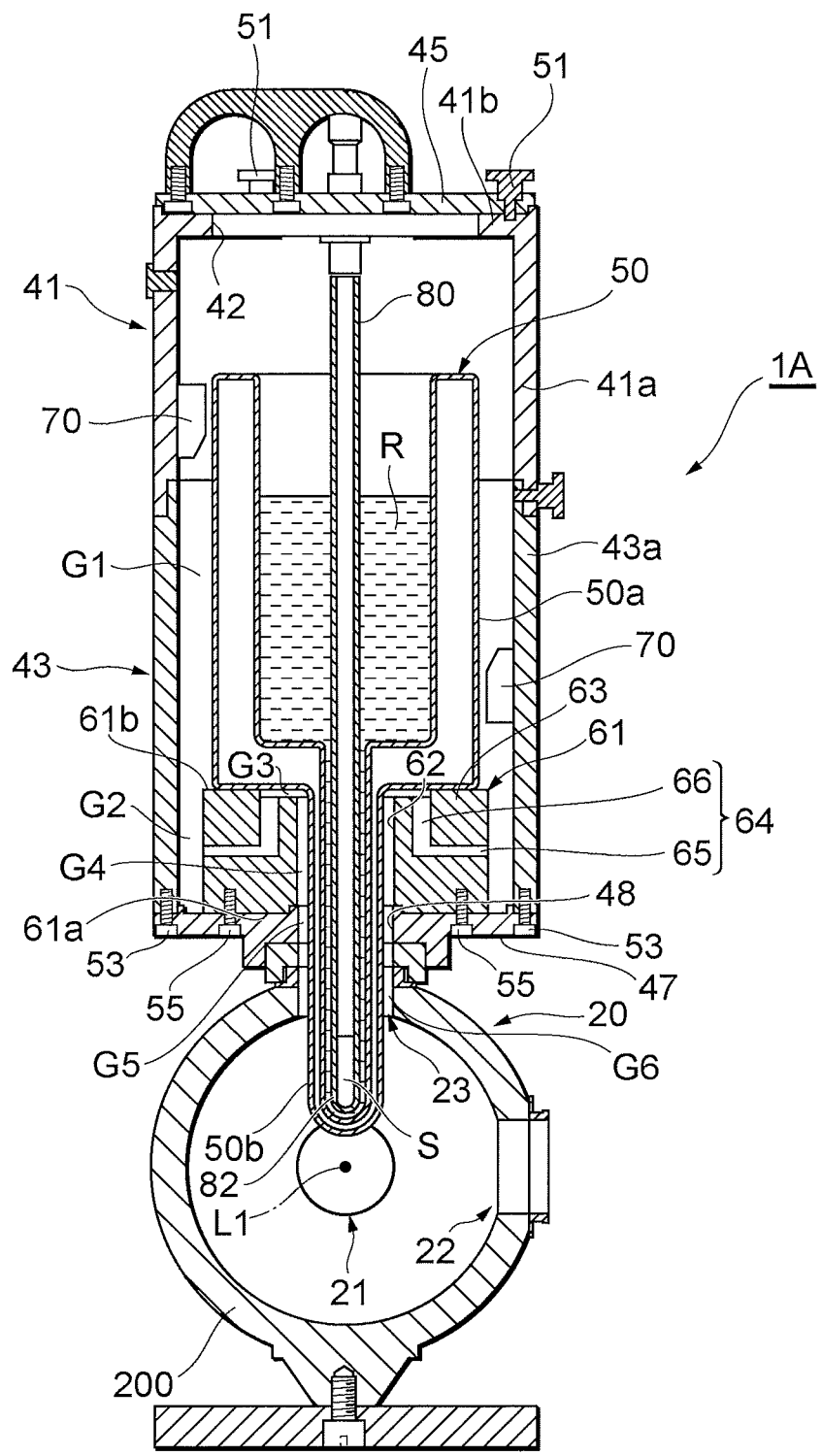
FIG. 9 is a sectional view showing an example of configurations of the integrating sphere, Dewar housing, and Dewar vessel.

Incidentally, the present embodiment allows the measurement in a state in which the sample S is regulated at a predetermined temperature by the medium R for regulation of temperature retained in the Dewar vessel 50, as shown in FIGS. 8 and 9. For example, if the medium R used is liquid nitrogen, the spectrometry of the sample S can be performed around the liquid nitrogen temperature (approximately −196° C.). In this manner, since the present embodiment employs the Dewar vessel 50 internally retaining the medium R so as to cover the sample S, the sample S can be easily regulated at a desired temperature.

In the present embodiment, the second container portion 50b retaining the medium R so as to cover the sample S is located so as to face the interior of the integrating sphere 20. For this reason, the temperature of the sample S can be regulated by the medium R, while suppressing influence on the sample S from an external ambience around the integrating sphere 20. Therefore, the sample S can also be efficiently regulated at a desired temperature.

In the present embodiment, the sample holding portion 82 and the sample S are located at the position away from the optical path L1, whereby the excitation light supplied from the entrance aperture 21 into the integrating sphere 20 is prevented from directly irradiating the sample S. The sample S is irradiated with the excitation light diffusely reflected on the internal surface 150 and the spectrometry is carried out with the light emitted from the sample S, as measured light. In this case, the sample S is irradiated with the excitation light diffusely reflected by the internal surface 150, whereby the light intensity of the excitation light to irradiate the sample S is reduced when compared with the case where the sample S is irradiated with the excitation light in the optical path L1. This reduces the light intensity of the measured light emitted from the sample S and thus controls the rate of light intensity of measured light leaking to the outside of the integrating sphere 20. Therefore, it is feasible to reduce the difference between the rates of leaking light quantities of the excitation light and the measured light and thus to inhibit the degradation of measurement accuracy of quantum yield.

The excitation light diffusely reflected irradiates the sample S to reduce the light intensity of the excitation light to irradiate the sample S, which can control the light intensity of excitation light returning to the entrance aperture 21 after diffusely reflected by the sample S.

In the present embodiment, the excitation light is diffusely reflected by the internal surface 150 of the integrating sphere body 200. In this case, the excitation light can be diffusely reflected without provision of a separate diffusely reflecting means except for the integrating sphere 20.

In the present embodiment, the second container portion 50b is located at the position away from the optical path L1. In this case, it is feasible to prevent the excitation light from being absorbed in the second container portion 50b and from being refracted to leak to the outside of the integrating sphere 20, in the optical path L1. Therefore, the degradation of measurement accuracy of quantum yield can be further suppressed.

The above described the preferred embodiment of the present invention, and it should be noted that the present invention is by no means intended to be limited to the foregoing embodiment but can be modified in various ways without departing from the spirit and scope of the invention.

Figure 10:
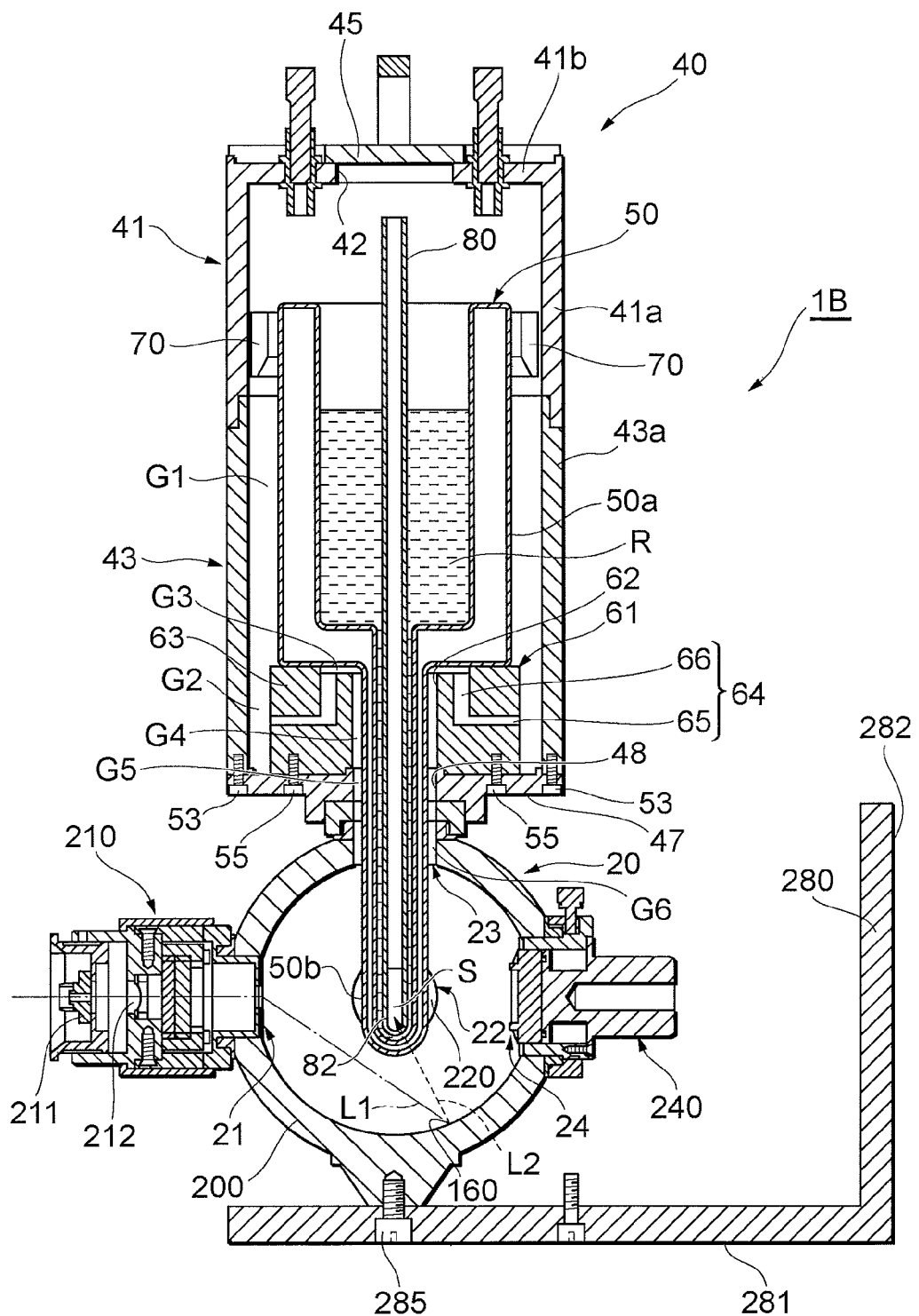
FIG. 10 is a sectional view showing an example of configurations of the integrating sphere, Dewar housing, and Dewar vessel.

In the present embodiment, the excitation light is diffusely reflected on the internal surface 150, but it may be diffusely reflected on another internal surface of the integrating sphere body 200. For example, a spectrometer 1B is configured, as shown in FIG. 10, to diffusely reflect the excitation light on an internal surface 160 (at a lower position in the drawing) opposed to the first sample introduction aperture 23, by changing the incidence angle of the optical path L1 at the entrance aperture 21. The diffusely reflected excitation light travels along an optical path L2 to irradiate the sample S. The tip portion of the second container portion 50b, the sample holding portion 82, and the sample S may be located at the center position of the integrating sphere body 200. In this case, luminescence from the sample S can be suitably measured because of symmetry of arrangement and structure of the sample S in the integrating sphere 20 or the like.

In the configuration example shown in FIG. 10, a second sample introduction opening 24 is provided in addition to the first sample introduction opening 23. The second sample introduction opening 24 is provided at a position opposite to the entrance aperture 21 on the other end side of the optical path L1 (i.e., at a right position in the drawing). A sample holder 240 for a sample S to be mounted thereon is attached to the second sample introduction opening 24.

The second sample introduction opening 24 and the sample holder 240 can be suitably used, for example, in the case where the sample S is a solid sample or a powder sample. In this case, the sample holder to be used is, for example, a sample holding substrate, a Petri dish, or the like. The sample holder 240, as well as the sample holder 80, is used depending upon types of sample S, contents of spectrometry, and so on. When the sample holder 240 is used, the integrating sphere 20 is set in a state in which the ground contact surface 282 of the mount 280 faces down so that a line connecting the entrance aperture 21 and the center position of the integrating sphere body 200 extends along a vertical line.

Figure 11:
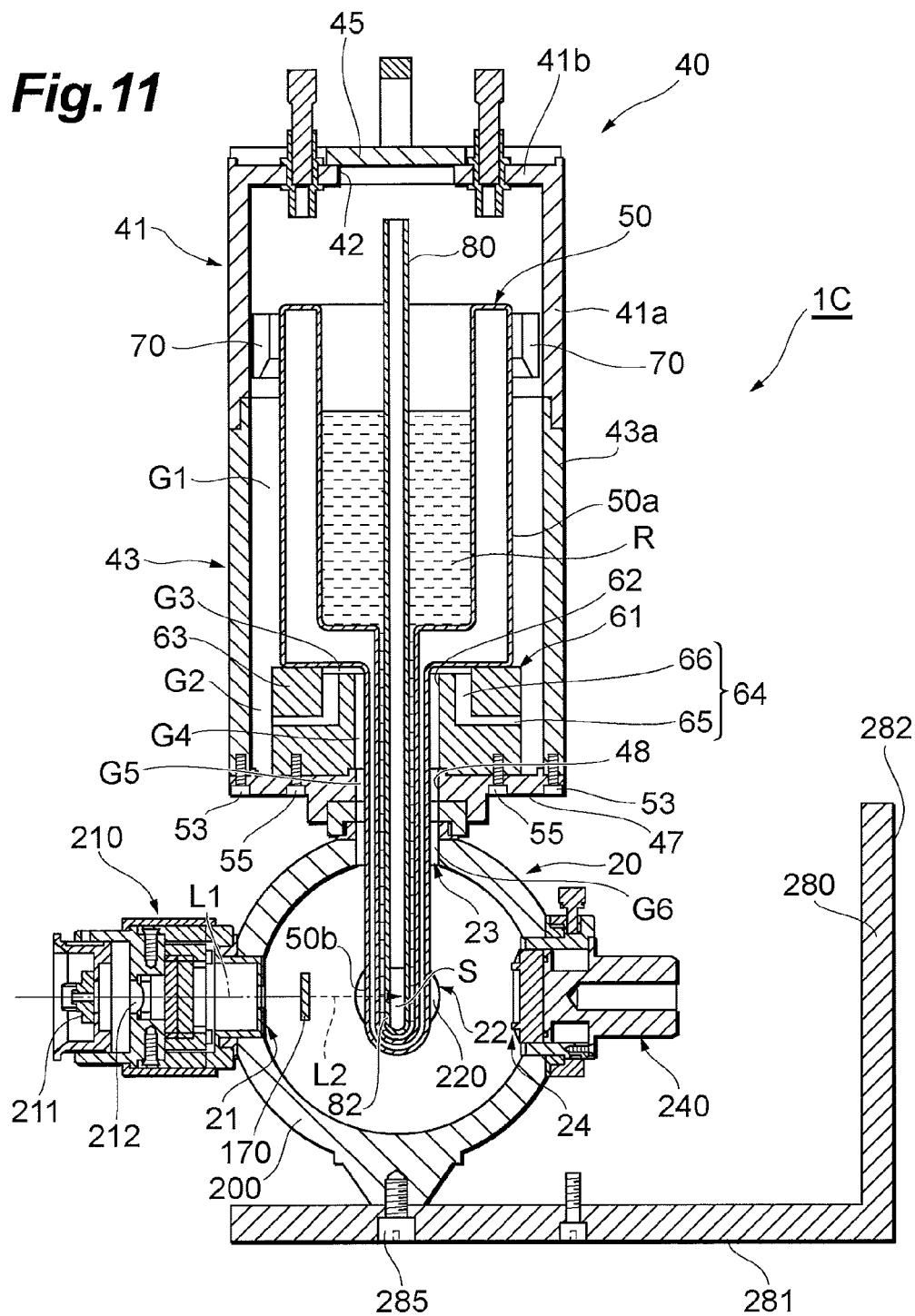
FIG. 11 is a sectional view showing an example of configurations of the integrating sphere, Dewar housing, and Dewar vessel.

In the present embodiment, the excitation light is diffusely reflected on the internal surface of the integrating sphere body 200, but the excitation light may be diffusely reflected using a diffuser plate. For example, in a spectrometer 1C, as shown in FIG. 11, the tip portion of the second container portion 50b, the sample holding portion 82, and the sample S are located at the center position of the integrating sphere body 200 and a diffuser plate 170 is arranged between the sample holding portion 82 and the entrance aperture 21. The excitation light travels along the optical path L1 to be diffusely reflected by the diffuser plate 170. The diffusely reflected excitation light travels along the optical path L2 to irradiate the sample S. In the configuration of FIG. 11, the spectrometer may be modified so that the incidence angle of the optical path L1 is changed at the entrance aperture 21, the excitation light is diffusely reflected by the diffuser plate 170 arranged in the optical path L1, and the diffusely reflected excitation light irradiates the sample S. When the excitation light is diffusely reflected with the use of the diffuser plate 170 in this manner, the excitation light can be easily diffusely reflected.

Figure 12:
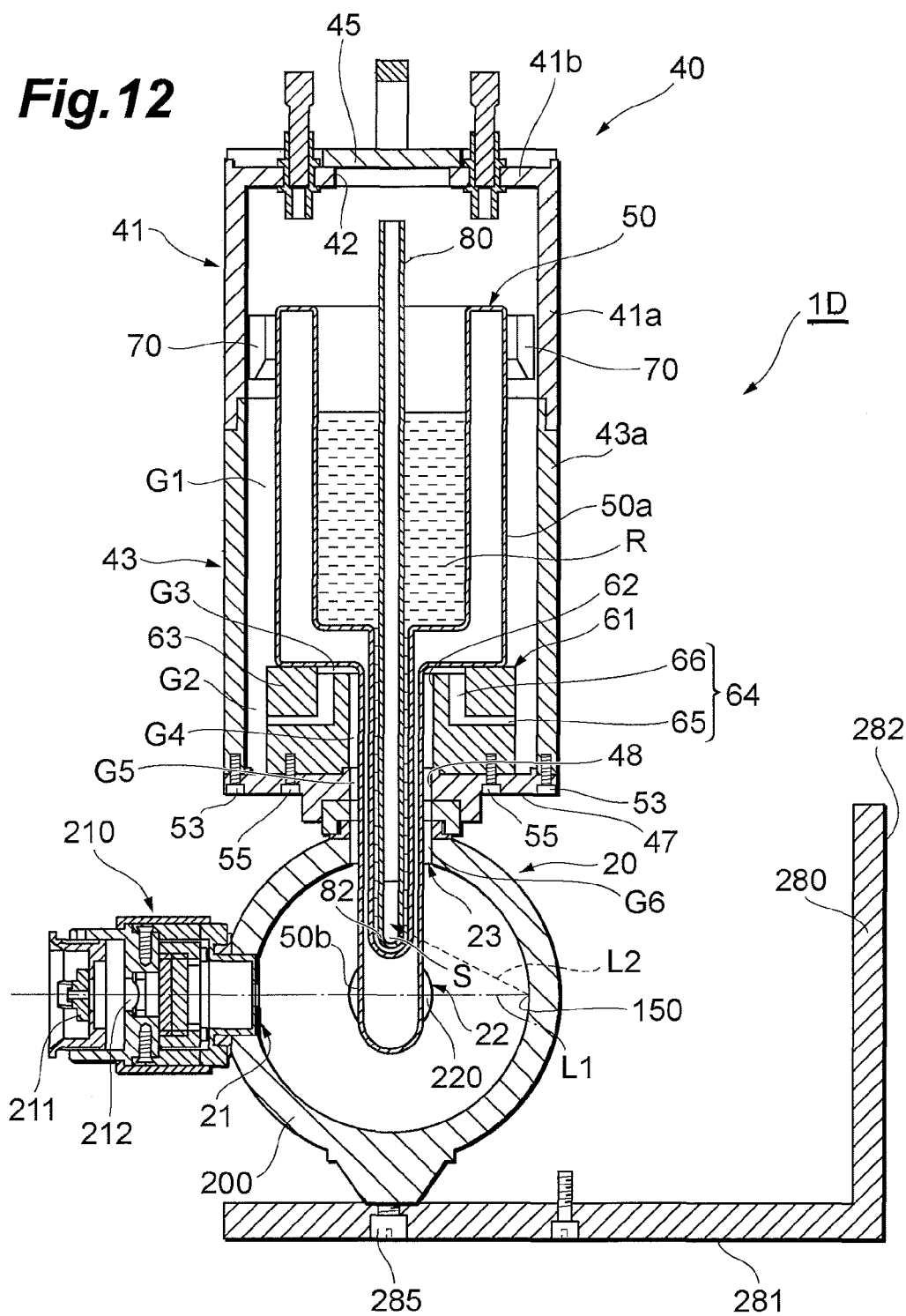
FIG. 12 is a sectional view showing an example of configurations of the integrating sphere, Dewar housing, and Dewar vessel.

In the present embodiment, the second container portion 50b is located at the position away from the optical path L1, but it may be located in the optical path L1. For example, in a spectrometer 1D, as shown in FIG. 12, the sample holding portion 82 and the sample S are located between the center position of the integrating sphere body 200 and the first sample introduction opening 23 and the tip portion of the second container portion 50b may be located at the center position of the integrating sphere body 200. In this case, the excitation light travels along the optical path L1 to pass through the second container portion 50b, and thereafter irradiates the internal surface 150 to be diffusely reflected on the internal surface 150. The diffusely reflected excitation light travels along the optical path L2 to irradiate the sample S. The tip portion of the second container portion 50b, the sample holding portion 82, and the sample S all may be located between the center position of the integrating sphere body 200 and the internal surface opposed to the entrance aperture 21.

Figure 13:
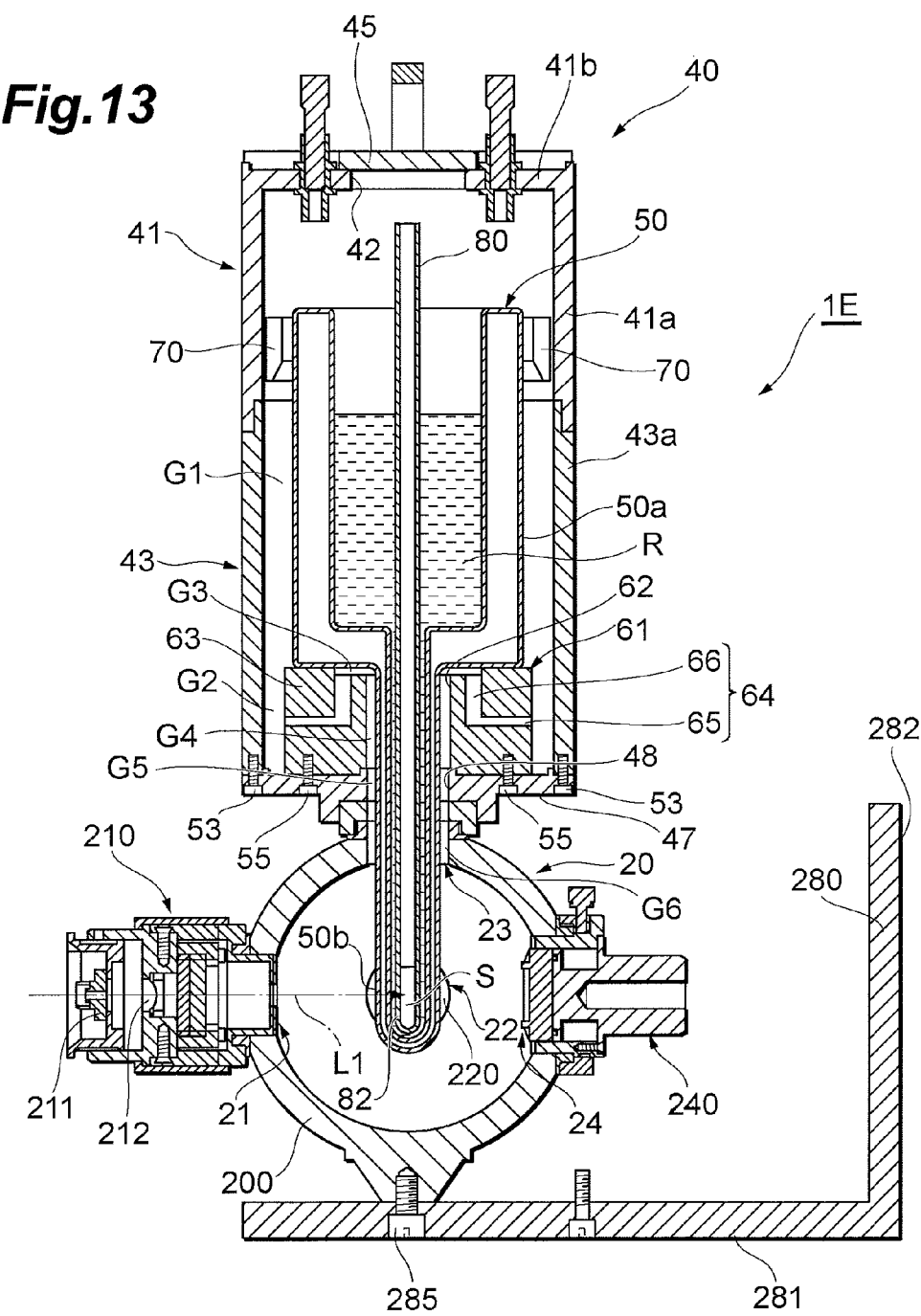
FIG. 13 is a sectional view showing an example of configurations of the integrating sphere, Dewar housing, and Dewar vessel.

In the present embodiment, the diffusely reflected excitation light irradiates the sample S, but the excitation light supplied from the entrance aperture 21 may directly irradiate the sample S. For example, in a spectrometer 1E, as shown in FIG. 13, the tip portion of the second container portion 50b, the sample holding portion 82, and the sample S are located at the center position of the integrating sphere body 200. The excitation light supplied from the entrance aperture 21 travels along the optical path L1 to directly irradiate the sample S. The spectrometer may also be configured so that the integrating sphere 20 is provided with the second sample introduction opening 24 and the excitation light directly irradiates the sample S arranged on the second sample introduction opening 24.

Figure 14:
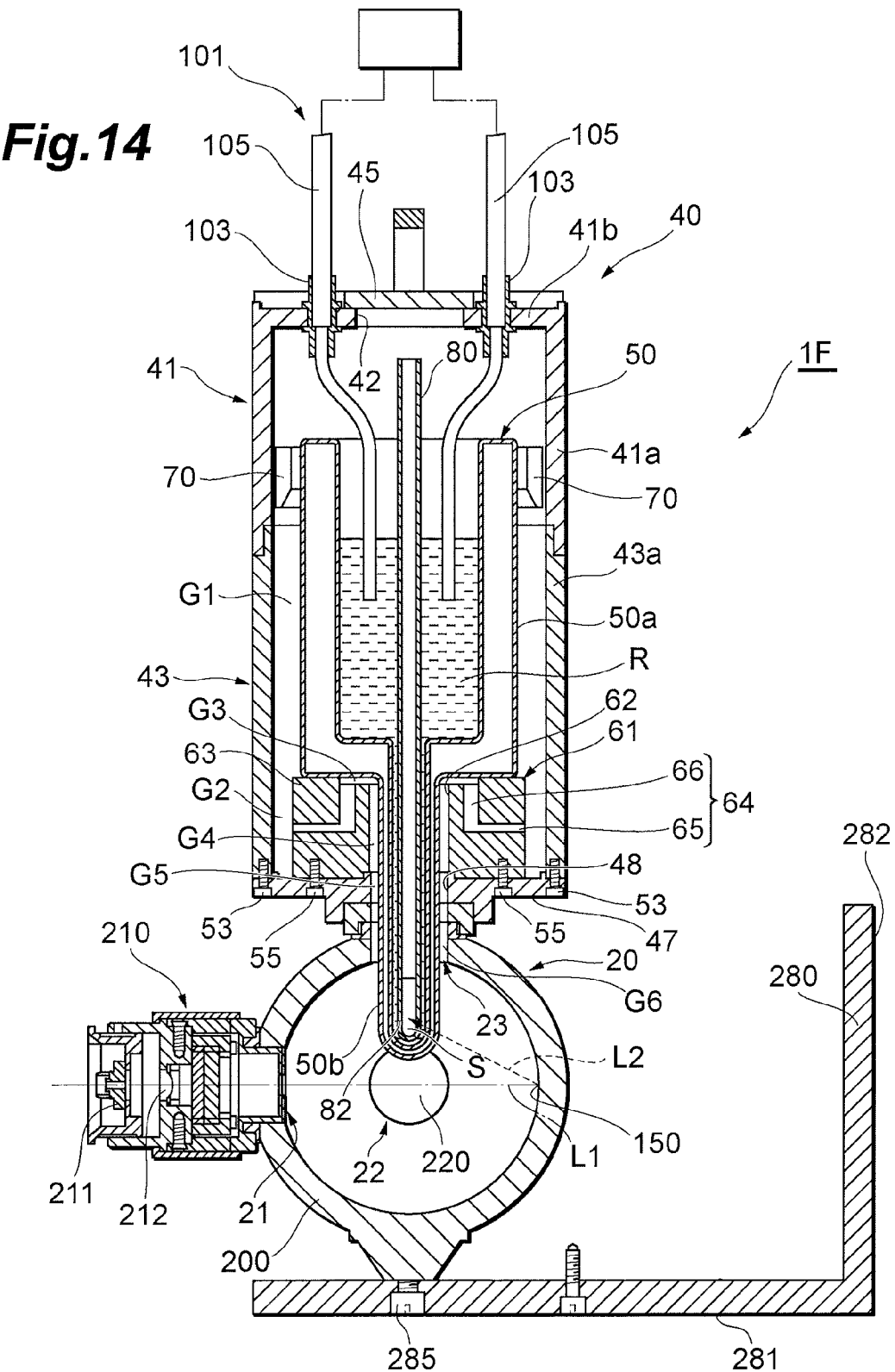
FIG. 14 is a sectional view showing an example of configurations of the integrating sphere, Dewar housing, and Dewar vessel.

In a spectrometer 1F, as shown in FIG. 14, the temperature of the medium R retained in the Dewar vessel 50 may be regulated by a chiller 101. In this case, the spectrometry of the sample S can be carried out at any temperature (e.g., about 0-60° C. in the case where the medium R is water). Connection to the chiller 101 can be implemented by providing the Dewar housing 40 (e.g., the first case 41 and the first lid plate 45) with tube connectors 103 and connecting tubes 105 to the respective tube connectors 103.

Table 1 show the measurement results of luminescence quantum yields with the foregoing spectrometers 1A, 1D, 1E and with the spectrometer different from 1E in that it is not provided with the Dewar vessel 50 and the medium R (which is represented by 1G in Table 1). The sample as a measurement target used was a solution obtained by diluting quinine sulfate with a solvent of sulfuric acid, and the sample holder used was a quartz tube. A quartz tube was used as a reference. The luminescence quantum yields were calculated according to Equation (1) below.

[Mathematical Image 1]

$$\text{Luminescence Quamtum Yeild} = \frac{I_{em}(\text{Sample}) - I_{em}(\text{Reference})}{I_{ex}(\text{Reference}) - I_{ex}(\text{Sample})} \quad (1)$$

$I_{em}$(Sample) and $I_{ex}$(Sample) represent the luminescence intensity and the intensity of excitation light after absorbed by the sample, respectively, obtained by measurement of a spectrum with the sample being set in the sample holder. $I_{em}$(Reference) and $I_{ex}$(Reference) represent the luminescence intensity and the intensity of excitation light, respectively, obtained by measurement of a spectrum with the reference being set in the sample holder.

TABLE 1

| Spectrometer | Luminescence Quantum Yield |
|---|---|
| 1A | 0.60 |
| 1D | 0.56 |
| 1E | 0.51 |
| 1G | 0.60 |

As shown in Table 1, the spectrometers 1A, 1D inhibit the degradation of measurement accuracy of luminescence quantum yield more than the spectrometer 1E does, because the sample S is irradiated with the diffusely reflected excitation light. The spectrometer 1A inhibits the degradation of measurement accuracy of luminescence quantum yield more than the spectrometer 1D does, because the second container portion 50b is located at the position away from the optical path L1. The spectrometer 1A provides the luminescence quantum yield equivalent to that of the spectrometer 1G without the Dewar vessel 50 and the medium R, though the second container portion 50b and the medium R are arranged in the optical path of the measured light emitted from the sample S.
Industrial Applicability The present invention is applicable to the spectrometer configured to apply the excitation light of a predetermined wavelength to the sample and to measure and evaluate the luminescence properties such as the fluorescence property of the sample by the photoluminescence method.
reference signs list 1A-1F spectrometer; 20 integrating sphere; 21 entrance aperture; 22 exit aperture; 23 first sample introduction opening; 40 Dewar housing; 50 Dewar vessel; 50b second container portion; 80 sample holder; 82 sample holding portion; 150, 160 internal surfaces; 170 diffuser plate; R medium for regulating temperature; S sample; L1, L2 optical paths.

The invention claimed is:
1. A spectrometer comprising:
an optical element configured to observe measured light emitted from a sample of a measurement target, the optical element having an internal surface defining an integrating space, the internal surface being covered with a high diffuse reflection material; and
a Dewar vessel which retains a medium for regulating temperature of the sample, so as to cover the sample and at least a portion of which is arranged in the integrating space.

2. The spectrometer according to claim 1, further comprising:
an irradiation light supply unit configured to supply excitation light into the integrating space;
a diffuse reflector configured to diffusely reflect the excitation light, as irradiated with the excitation light in the integrating space; and
a sample holder which has a portion holding the sample and which is disposed inside the Dewar vessel so as to locate said portion holding the sample in the integrating space,
wherein the optical element has an entrance aperture configured to input the excitation light thereinto, and
wherein said portion of the sample holder holding the sample is disposed away from an optical path of the excitation light between the entrance aperture and the diffusely reflector and is irradiated with the excitation light diffusely reflected by the diffusely reflector.

3. The spectrometer according to claim 2,
wherein the diffusely reflector is formed by the high diffuse reflection material on the internal surface.

4. The spectrometer according to claim 2, wherein said at least a portion of the Dewar vessel is disposed away from the optical path.

5. The spectrometer according to claim 4,
wherein the sample holder is a tubular member closed at one end.

6. The spectrometer according to claim 5,
wherein the Dewar vessel has a first container portion having a first inside diameter and located on the other end side, and a second container portion having a second inside diameter smaller than the first inside diameter and located on one end side, and
wherein the second inside diameter is set larger than an outside diameter of the sample holder.

7. The spectrometer according to claim 6, further comprising:
a Dewar housing having first and second cases of a tubular shape and housing the Dewar vessel, and
wherein the Dewar vessel is radially positioned by a plurality of spacers disposed at predetermined intervals on internal peripheral surfaces of the first and the second cases, the spacers form a predetermined first gap between internal peripheral surfaces of the first and the second cases and an external peripheral surface of the first container portion.

8. The spectrometer according to claim 7, further comprising:
a support pedestal supporting the Dewar vessel, and
wherein the Dewar housing further has a first lid plate detachably attached to a bottom portion of the first case and a second lid plate detachably attached to one end of the second case,
wherein the support pedestal is detachably attached to the second lid plate,
wherein the support pedestal is provided with a projecting portion projecting from a second surface, on the second surface opposed to a first surface attached to the second lid plate, and
wherein the projecting portion is in contact with the Dewar vessel to define a position of the Dewar vessel in an insertion direction thereof.

9. The spectrometer according to claim 2,
wherein the entrance aperture is configured to change the incidence angle of the optical path so that said portion of the sample holder holding the sample is disposed away from the optical path.

10. The spectrometer according to claim 1, further comprising:
an irradiation light supply unit configured to supply excitation light into the integrating space; and
a diffuse reflector configured to diffusely reflect the excitation light,
wherein the optical element has an entrance aperture configured to input the excitation light thereinto, and
wherein the diffuse reflector is a diffuser plate which is arranged so as to receive the excitation light from the entrance aperture and diffusely reflects the excitation light.

11. The spectrometer according to claim 1,
wherein the Dewar vessel is a nearly tubular container closed at one end and is constructed in a heat-insulated double structure with a vacuum layer, the Dewar vessel has a first container portion having a first inside diameter and located on the other end side, and a second container portion having a second inside diameter smaller than the first inside diameter and located on one end side.

12. The spectrometer according to claim 11, further comprising:
a support pedestal supporting the Dewar vessel, and
wherein a length of the second container portion is set so that a tip portion of the second container portion projects by a predetermined length into the integrating space in a state in which the Dewar vessel is in contact with a contact surface of the support pedestal.

13. The spectrometer according to claim 12,
wherein the optical element has a light integrator body, the optical element is provided with a first sample introduction opening configured to introduce the sample into the integrating space, and
wherein the length of the second container portion is set so that the tip portion of the second container portion is located between a center position of the optical element and the first sample introduction opening.

14. The spectrometer according to claim 1, further comprising:
an irradiation light supply unit configured to supply excitation light into the integrating space; and
a diffusely reflector configured to diffusely reflect the excitation light, and
wherein the optical element has an entrance aperture configured to input the excitation light into the integrating space, and
wherein at least the portion of Dewar vessel is disposed away from an optical path of the excitation light between the entrance aperture and the diffusely reflector and is irradiated with the excitation light diffusely reflected by the diffusely reflector.

15. The spectrometer according to claim 14,
wherein the entrance aperture is configured to change the incidence angle of the optical path so that said portion of the sample holder holding the sample is disposed away from the optical path.

16. The spectrometer according to claim 1,
wherein the optical element is an integrating sphere.

* * * * *

UNITED STATES PATENT AND TRADEMARK OFFICE
CERTIFICATE OF CORRECTION

| | |
|---|---|
| PATENT NO. | : 8,587,779 B2 |
| APPLICATION NO. | : 13/126523 |
| DATED | : November 19, 2013 |
| INVENTOR(S) | : Kazuya Iguchi and Kengo Suzuki |

It is certified that error appears in the above-identified patent and that said Letters Patent is hereby corrected as shown below:

On the title page item (73) "Assignee"

change "Hamamatsu-shi, Shizoka (JP)" to --Hamamatsu-shi, Shizuoka (JP)--

Signed and Sealed this
Eleventh Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,587,779 B2
APPLICATION NO.  : 13/126523
DATED            : November 19, 2013
INVENTOR(S)      : Iguchi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 38 days.

Signed and Sealed this
Twenty-second Day of September, 2015

Michelle K. Lee
*Director of the United States Patent and Trademark Office*